United States Patent
Azorsa

(10) Patent No.: US 9,850,303 B2
(45) Date of Patent: Dec. 26, 2017

(54) HYBRIDOMA CLONES AND MONOCLONAL ANTIBODIES TO TETRASPANIN 8

(71) Applicant: The Translational Genomics Research Institute, Phoenix, AZ (US)

(72) Inventor: David Azorsa, Phoenix, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 170 days.

(21) Appl. No.: 14/776,475

(22) PCT Filed: Mar. 17, 2014

(86) PCT No.: PCT/US2014/030820
§ 371 (c)(1),
(2) Date: Sep. 14, 2015

(87) PCT Pub. No.: WO2014/145961
PCT Pub. Date: Sep. 18, 2014

(65) Prior Publication Data
US 2016/0039931 A1   Feb. 11, 2016

Related U.S. Application Data

(60) Provisional application No. 61/788,177, filed on Mar. 15, 2013.

(51) Int. Cl.
*C12N 5/20* (2006.01)
*C07K 16/00* (2006.01)
*C07K 16/28* (2006.01)
*C07K 17/00* (2006.01)
*G01N 33/532* (2006.01)

(52) U.S. Cl.
CPC ........... *C07K 16/28* (2013.01); *G01N 33/532* (2013.01); *C07K 2317/14* (2013.01); *C07K 2317/34* (2013.01)

(58) Field of Classification Search
None
See application file for complete search history.

(56) References Cited

U.S. PATENT DOCUMENTS

| | | | | |
|---|---|---|---|---|
| 5,668,002 A | * | 9/1997 | Linnenbach | C07K 14/705 435/325 |
| 5,786,163 A | * | 7/1998 | Hall | C07K 14/58 435/7.92 |
| 9,040,671 B2 | * | 5/2015 | Rubinstein | C07K 16/28 530/387.3 |
| 9,487,586 B2 | * | 11/2016 | Rubinstein | C07K 16/28 |
| 2011/0045603 A1 | * | 2/2011 | Guo | C07K 14/47 436/501 |

OTHER PUBLICATIONS

Guo Q, Xia B, Zhang F, Richardson MM, Li M, et al. (2012) Tetraspanin CO-029 Inhibits Colorectal Cancer Cell Movement by Deregulating Cell-Matrix and Cell-Cell Adhesions. PLoS ONE 7(6): e38464, Jun. 5, 2012.*

Azorsa et al. A general approach to the generation of monoclonal antibodies against members of the tetraspanin superfamily using recombinant GST fusion proteins. Journal of Immunological Methods 229 (1999) 35-48.*

Sela, et al., "Colon Carcinoma-Associated Glycoproteins Recognized by Monoclonal Antibodies CO-029 and GA22-2," Hybridoma, vol. 8, No. 4, 1989.*

Hemler, ME. Targeting of tetraspanin proteins—potential benefits and strategies. Nat Rev Drug Discov. Sep. 2008 ; 7(9): 747-758.*

Azorsa, et al. A General Approach to the Generation of Monoclonal Antibodies Against Members of the Tetraspanin . . . Journal of Immunilogical Methods 1999, 229(1-3):35-48; Abstr.

Jefferis, et al. Human Immunoglobulin Allotypes: Possible Implications for Immunogenicity. MAbs 2009, 1(4):332-338; p. 2, col. 2, p. 4, col. 2.

UniProt Direct Submissions P19075. TSN8_Human. (Mar. 6, 2013) (Retrieved from the Internet Aug. 3, 2014: <http://www.uniprot.org/uniprot/P19075.txt?version=116>]; p. 1.

* cited by examiner

*Primary Examiner* — Maher Haddad

(57) ABSTRACT

The present invention is directed to a monoclonal antibody that recognizes human TSPAN8 in its native form. The invention is also directed to a hybridoma cell line that produces the monoclonal antibody, and exosome purification kits using the antibody.

19 Claims, 5 Drawing Sheets

HYBRIDOMA CLONES AND MONOCLONAL ANTIBODIES TO TETRASPANIN 8

CROSS-REFERENCE TO RELATED APPLICATIONS

The present application is the national stage of International Patent Application No. PCT/US2014/030820, filed on Mar. 17, 2014, which claims priority to U.S. Application No. 61/788,177, filed Mar. 15, 2013, the entire contents and disclosure of which are herein incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 4 3.24 kilobyte ASCII (text) file named "TSPAN8SEQ371" created on Sep. 9, 2015.

FIELD OF THE INVENTION

This application relates to hybridoma clones and monoclonal antibodies, and more particularly, hybridoma clones and monoclonal antibodies directed to Tetraspanin 8 protein and methods of use.

BACKGROUND OF THE INVENTION

Tetraspanins are small membrane-bound proteins that are expressed in species ranging from sponges to mammals, with each organism expressing a large number of tetraspanin family members. A. Garcia-Espana et al., *Appearance of new tetraspanin genes during vertebrate evolution*, Genomics (91), 326-334 (2008). Tetraspanins are typically involved in multiple biological processes, such as fertilization, parasite and viral infection, synaptic contacts at neuromuscular junctions, platelet aggregation, maintenance of skin integrity, immune response induction, metastasis suppression, and tumor progression. Tetraspanins cross the membrane four times, but not all four-transmembrane molecules are tetraspanins. In general, tetraspanins have short amino- and carboxy-terminal tails, a small intracellular loop between transmembrane region 2 (TM2) and TM3, a small extracellular loop (EC1) between TM1 and TM2 and a large extracellular loop (EC2) between TM3 and TM4, as illustrated in FIG. 1. See M. Zoller, *Tetraspanins: push and pull in suppressing and promoting metastasis*, Nature Reviews Cancer (9) 40-55 (2009).

In addition to having these various functionalities within the cell and at the cell membrane, large numbers of tetraspanins are also released from the cell in exosomes. A. Lakkaraju & E. Rodriguez-Boulan, *Itinerant exosomes: emerging roles in cell and tissue polarity*, Trends Cell Biol. (18), 199-209 (2008). Exosomes, 30-100 nm vesicles, are released by many cells. J. S. Schorey & S. Bhatnagar, *Exosome function: from tumor immunology to pathogen biology*, Traffic (9) 871-881 (2008). Exosomes derive from multivesicular bodies, which either fuse with lysosomes or fuse with the plasma membrane and release their intraluminal vesicles as exosomes. The molecular composition of exosomes reflects their origin from intraluminal vesicles and includes several tetraspanins. Id. Exosomal proteins maintain their functional activity, as shown by their capacity to present peptides in major histocompatibility complex class I and II molecules. Id. Exosomes are thought to constitute a potent mode of intercellular communication that is important in the immune response, cell-to-cell spread of infectious agents, and tumour progression. Tetraspanins and their associated proteins are enriched in exosomes. Although the contribution of tetraspanins to the make-up of exosomes is well known, their impact on the functions of exosomes has not been determined. However, some current research has shown that, potentially, a blockage of angiogenesis-initiating exosomes from tumors may hinder tumor vascularization and thrombosis. I. Nazarenko et al., *Cell Surface Tetraspanin TSPAN8 Contributes to Molecular Pathways of Exosome-Induced Endothelial Cell Activation*, Cancer Research (70) 1668-1678 (2010); see also H. G. Zhang & W. E. Grizzle, *A Novel Pathway of Local and Distant Intracellular Communication that Facilitates the Growth and Metastasis of Neoplastic Lesions*, American Journal of Pathology (184) 28-41 (2014).

Tetraspanin 8 (TSPAN8), otherwise known as CO-029, regulates cell motility and cell survival and is generally involved in the promotion of angiogenesis. Moreover, evidence exists that TSPAN8 promotes motility mostly through its association with α6β4 integrin. Research has shown that the interaction between TSPAN8 and α6β4 integrin induce changes in cell shape towards a migratory phenotype, increased motility, and hepatic metastasis formation. S. Huerta et al., *Gene expression profile of metastatic colon cancer cells resistant to cisplatin-induced apoptosis*, International Journal of Oncology (22) 663-670 (2003) and M. Herlevsen et al., *The association of the Tetraspanin D6.1A with the α6β4 integrin supports cell motility and liver metastasis formation*, Journal of Cell Biology (116) 4373-4390 (2003).

TSPAN8 has been reported to have a role in cancer. In particular, overexpression of TSPAN8 was originally noted in colorectal cancer and was subsequently identified in pancreatic cancer and hepatocellular carcinoma. M. Zoller, *Gastrointestinal tumors: metastasis and tetraspanins*, Gastroenterology (44) 573-586 (2006). In particular, TSPAN8 overexpression generally correlates with poor differentiation and intrahepatic spread of hepatoma and only a hepatoma clone that overexpresses TSPAN8 develops metastases. K. Kanetaka et al., *Possible involvement of tetraspanin CO-029 in hematogenous intrahepatic metastasis of liver cancer cells*, Journal of Gastroenterology and Hepatology (18) 1309-1314 (2003). In addition, increased TSPAN8 expression in a metastasis versus the primary tumor-derived colon carcinoma line further supports a role in tumor progression. S. Huerta et al., *Gene expression profile of metastatic colon cancer cells resistant to cisplatin-induced apoptosis*, International Journal of Oncology (22) 663-670 (2003). Furthermore, research has also shown that high expression levels of TSPAN8 are associated with increased resistance to apoptosis. S. Huerta et al., *Gene expression profile of metastatic colon cancer cells resistant to cisplatin-induced apoptosis*, International Journal of Oncology (22) 663-670 (2003) and S. Kuhn et al., *A complex of EpCAM, claudin-7, CD44 variant isoforms, and tetraspanins promotes colorectal cancer progression*, Molecular Cancer Research (5) 553-567 (2007). Other research has shown a similar relationship between increased expression of TSPAN8 and multiple forms of cancer. Q. Guo et al., *Tetraspanin CO-029 inhibits Colorectal Cancer Cell Movement by Deregulating Cell-Matrix and Cell-Cell Adhesions*, PLoS One (7) e38464 (2012) and O. Berthier-Vergnes et al., *Gene expression profiles of human melanoma cells with different invasive potential reveal TSPAN8 as a novel mediator of invasion*, British Journal of Cancer (104) 155-165 (2011). All references recited above and herein are hereby incorporated by reference in their entireties for any and all purposes.

A need exists for anti-TSPAN8 antibodies having unique genetic and amino acid structures, including unique binding and functional characteristics. The development of new anti-TSPAN8 monoclonal antibodies and hybridoma cells lines that produce such monoclonal antibodies would be a valuable tool for the effective diagnosis of various diseases and use in other biomedical techniques.

SUMMARY

Some embodiments of the invention include antibodies and fragments thereof that bind to TSPAN8. The invention is also directed to one or more hybridoma cell lines that produce the one or more antibodies that specifically bind to TSPAN8, and to methods of using the antibodies. In some embodiments, the antibodies are monoclonal antibodies. Moreover, in some embodiments, the monoclonal antibodies recognize the native, non-reduced TSPAN8 polypeptide.

Some embodiments of the invention include antibodies and fragments thereof that bind to native TSPAN8 polypeptide or a fragment thereof. For example, at least some of the antibodies specifically bind to a TSPAN8 polypeptide of SEQ ID NO:1. In other aspects, at least some of the antibodies binds to TSPAN8 polypeptides or fragments thereof that comprise SEQ ID NO:2.

The antibodies of the present invention are preferably isolated monoclonal antibodies having specific binding properties against a human TSPAN8 protein, more preferably against human TSPAN8 in its native, non-reduced form. The antibodies may be labeled with one or more labels selected from the group consisting of a biotin label, a fluorescent label, an enzyme label, a coenzyme label, a chemiluminescent label, and a radioactive isotope label.

Some embodiments of the invention include a monoclonal antibody that is produced by one or more hybridoma cell lines. For example, the invention includes a monoclonal antibody comprising the same epitope specificity as a monoclonal antibody produced by hybridoma cell line BT-43, which has been deposited with the ATCC.

Some embodiments of the invention include one or more kits. For example, the invention can include an exosome purification kit that includes at least one container that contains monoclonal antibodies that specifically bind to human TSPAN8. The antibodies in the exosome purification kit may be labeled with one or more labels selected from the group consisting of a biotin label, a fluorescent label, an enzyme label, a coenzyme label, a chemiluminescent label, and a radioactive isotope label.

Additional objectives, advantages and novel features will be set forth in the description which follows or will become apparent to those skilled in the art upon examination of the drawings and detailed description which follows.

BRIEF DESCRIPTION OF THE DRAWINGS

Illustrative and exemplary embodiments of the invention are shown in the drawings in which.

DETAILED DESCRIPTION OF THE INVENTION

Figure 1:
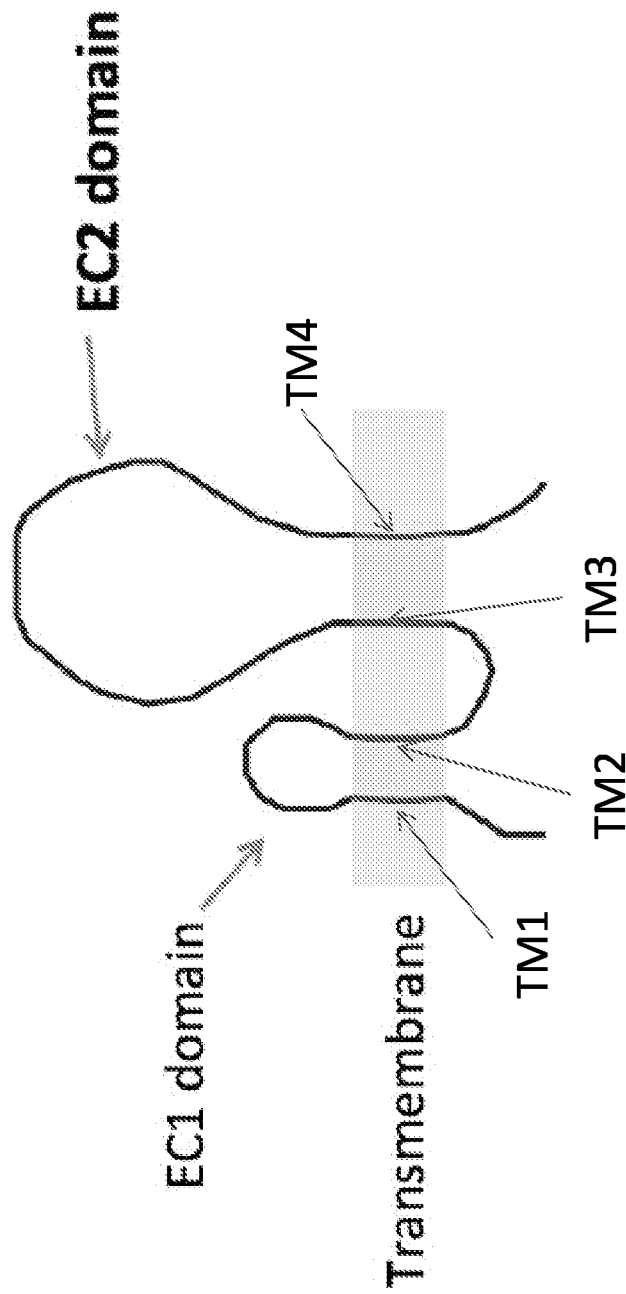
FIG. 1 is a simplified illustration of the TSPAN8 protein positioned through a cell membrane.

The present invention is directed to an antibody that recognizes human tetraspanin 8 (TSPAN8). The invention is also directed to a hybridoma cell line that produces the antibody, and to methods of using the antibody. More specifically, the inventors produced a murine hybridoma clone that secretes murine monoclonal antibodies to the human TSPAN8 protein that is designated BT-43. The anti-TSPAN8 monoclonal antibodies recognize human TSPAN8 in its native form. In some embodiments of the invention, the anti-TSPAN8 monoclonal antibody recognizes native human TSPAN8 in its native, non-reduced form.

The term "antibody" is used herein in the broadest sense and refers generally to a molecule that contains at least one antigen binding site that immunospecifically binds to a particular antigen target of interest. The term "antibody" thus includes but is not limited to native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. The term "antibody," thus, includes full length antibodies and/or their variants, as well as fragments thereof. Binding of an antibody to a target can cause a variety of effects, such as but not limited to where such binding modulates, decreases, increases, antagonizes, agonizes, mitigates, alleviates, blocks, inhibits, abrogates and/or interferes with at least one target activity or binding, or with receptor activity or binding, in vitro, in situ, and/or in vivo. The present invention, thus, encompasses antibody fragments capable of binding to a biological molecule (such as an antigen or receptor) or portions thereof, including but not limited to Fab, Fab' and F(ab')$_2$, facb, pFc', Fd, Fv or scFv fragments. (See, e.g., CURRENT PROTOCOLS IN IMMUNOLOGY, (Colligan et al. eds., John Wiley & Sons, Inc., NY, 1994-2001)); diabodies; linear antibodies (Zapata et al. (1995) Protein Eng. 8(10):1057); single-chain antibody molecules; and multispecific antibodies formed from antibody fragments.

Accordingly, antibody is used in the broadest sense and specifically covers, for example, single anti-TSPAN8 monoclonal antibodies (including agonist, antagonist, and neutralizing antibodies), anti-TSPAN8 antibody compositions with polyepitopic specificity, single chain anti-TSPAN8 antibodies, and fragments of anti-TSPAN8 antibodies. The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibody may be abbreviated "mAb."

"Fv" is the minimum antibody fragment that contains a complete antigen-recognition and antigen-binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the VH and VL domains of antibody, wherein these domains are present in a single polypeptide chain. Preferably, the Fv polypeptide further comprises a polypeptide linker between the $V_H$ and $V_L$ domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) Proc. Natl. Acad. Sci. USA 90:6444.

An "isolated" antibody is one that has been identified and separated and/or recovered from a component of its natural environment. Contaminant components of its natural environment are materials, which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A "native sequence TSPAN8 polypeptide" or "native sequence TSPAN8 protein" comprises a polypeptide having the same amino acid sequence as the corresponding TSPAN8 polypeptide derived from nature. Such native sequence TSPAN8 polypeptides can be isolated from nature or can be produced by recombinant or synthetic methods. The term "native sequence TSPAN8 polypeptide" specifically encompasses naturally-occurring truncated, secreted, and/or membrane-bound forms of the specific TSPAN8 polypeptide (e.g., an extracellular domain sequence), naturally-occurring variant forms (e.g., alternatively spliced forms) and naturally-occurring allelic variants of the polypeptide. In various embodiments of the invention, the native sequence TSPAN8 polypeptides disclosed herein are mature or full-length native sequence polypeptides comprising the full-length amino acid sequences recited herein. In some embodiments, the "native sequence TSPAN8 polypeptide" comprises an amino acid sequence of SEQ ID NO:1 or a fragment thereof. Moreover, in some embodiments, the "native sequence TSPAN8 polypeptide" comprises a fragment of the full-length polypeptide or protein, such as an amino acid of SEQ ID NO:2. Significantly, SEQ ID NO:2 is a fragment itself of SEQ ID NO:1 (representing amino acids 110-205 of SEQ ID NO:1).

The terms "individual," "subject," and "patient," used interchangeably herein, refer to an animal, preferably a mammalian (including a non-primate and a primate), including, but not limited to, murines, simians, humans, mammalian farm animals (e.g., bovine, porcine, ovine), mammalian sport animals (e.g., equine), and mammalian pets (e.g., canine and feline); preferably the term refers to humans.

As used herein, the terms "treatment", "treating", and the like, refer to obtaining a desired pharmacologic, and/or physiologic effect. The effect may be therapeutic in terms of a partial or complete cure for a disease and/or adverse effect attributable to the disease. "Treatment," as used herein, includes administration of a compound of the present invention for treatment of a disease or condition in a mammal, particularly in a human, and includes: (a) inhibiting the disease, i.e., arresting its development; (b) providing palliative care, i.e., reducing and preventing the suffering of a patient; and (c) relieving the disease, i.e., causing regression of the disease or disorder or alleviating symptoms or complications thereof. Dosage regimens may be adjusted to provide the optimum desired response.

As used herein, the term "epitope" refers to a portion of an antigenic molecule to which an antibody is produced and to which the antibody will bind. A "TSPAN8 epitope" comprises the part of the TSPAN8 protein to which an anti-TSPAN8 monoclonal antibody specifically binds. Epitopes can comprise linear amino acid residues (i.e., residues within the epitope are arranged sequentially one after another in a linear fashion), nonlinear amino acid residues, or both linear and nonlinear amino acid residues. Typically epitopes are generally short amino acid sequences (e.g. about five amino acids in length).

Monoclonal Antibodies

The anti-TSPAN8 antibodies may, alternatively, be monoclonal antibodies. Monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

An immunizing agent typically includes the TSPAN8 polypeptide, a portion thereof, a fusion protein thereof, and/or a whole fixed or living cell (e.g., LoVo cells that express TSPAN8). Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding (1986) Monoclonal Antibodies: Principles and Practice, Academic Press, pp. 59-103). Immortalized cell lines may be transformed mammalian cells, particularly myeloma cells of rodent, bovine, and human origin. Rat or mouse myeloma cell lines may be employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor (1984) J. Immunol. 133:3001; Brodeuretal (1987) Monoclonal Antibody Production Techniques and Applications, Marcel Dekker, Inc., New York, pp. 51-631).

The culture medium in which the hybridoma cells are cultured can then be assayed for the presence of monoclonal antibodies directed against TSPAN8 or a fragment thereof. The binding specificity of monoclonal antibodies produced by the hybridoma cells can be determined by inmunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard (1980) Anal. Biochem. 107:220.

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures, such as, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof can be accomplished using routine techniques known in the art.

The anti-TSPAN8 monoclonal antibodies of the invention may be whole or an antigen-binding fragment of the antibody that specifically binds a TSPAN8 polypeptide, preferably a native sequence TSPAN8 polypeptide (e.g., a TSPAN8 polypeptide of SEQ ID NO:1 or a fragment thereof, such as SEQ ID NO:2). Furthermore, in a preferred embodiment the monoclonal antibody is identified as lab number mAb BT-43 having recognition of a TSPAN8 protein from at least cell line.

In one non-limiting embodiment the monoclonal antibody is produced by a hybridoma cell line, such that the antibody or functional fragment thereof binds to a TSPAN8 protein or a fragment thereof. In one embodiment, the monoclonal antibody is of a murine IgG1, kappa chain isotype.

More specifically, the monoclonal antibody of the invention comprises a heavy chain variable region (HCVR) and a light chain variable region (LCVR), wherein said HCVR comprises: a) a peptide at CDRH1, b) a peptide at CDRH2, c) a peptide at CDRH3, and wherein said LCVR comprises: a) a peptide at CDRL1, b) a peptide at CDRL2, and c) a peptide at CDRL3.

Human and Humanized Antibodies

The murine monoclonal antibodies of the present invention can be humanized to reduce the immunogenicity for use in humans. Humanized forms of non-human (e.g., murine)

antibodies are chimeric immunoglobulins, immunoglobulin chains or fragments thereof (such as, Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues, which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al. (1986) Nature 321:522; Riechmann et al. (1988) Nature 332:323; and, Presta (1992) Curr. Op. Struct. Biol. 2:593).

Methods for humanizing non-human antibodies are well known in the art. An example approach is to make mouse-human chimeric antibodies having the original variable region of the murine monoclonal antibodies, joined to constant regions of a human immunoglobulin. Chimeric antibodies and methods for their production are known in the art. See, e.g., Cabilly et al. European Patent EP0125023 (published Nov. 14, 1984); Taniguchi et al., European Patent EP0171496 (published Feb. 19, 1986); Morrison et al., European Patent Application EP0173494 (published Jan. 18, 1986); Neuberger et al., International Publication No. WO/1986/01533, (published Mar. 13, 1986); Kudo et al., European Patent Application EP0184187 (published Jun. 11, 1986); Robinson et al., International Publication No. WO/1987/002671 (published May 7, 1987); Liu et al. (1987) Proc. Natl. Acad. Sci. USA 84: 3439-3443; Sun et al. (1987) Proc. Natl. Acad. Sci. USA 84: 214-218; Better et al. (1988) Science 240: 1041-1043. These references are incorporated herein by reference. Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes.

Generally, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al. (1986) Nature, 321:522-525; Riechmann et al. (1988) Nature, 332:323-327; Verhoeyen et al. (1988) Science, 239:1534-1536), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Pharmaceutical Compositions of Antibodies

In other embodiments there is provided a pharmaceutical composition including an antibody or fragment as described above together with a pharmaceutically acceptable carrier, diluent or excipient.

In the preparation of the pharmaceutical compositions comprising the antibodies described in the teachings herein, a variety of vehicles and excipients and routes of administration may be used, as will be apparent to the skilled artisan. Representative formulation technology is taught in, inter alia, Remington: The Science and Practice of Pharmacy, 19th Ed., Mack Publishing Co., Easton, Pa. (1995) and Handbook of Pharmaceutical Excipients, 3rd Ed, Kibbe, A. H. ed., Washington D.C., American Pharmaceutical Association (2000); hereby incorporated by reference in their entirety.

The pharmaceutical compositions will generally comprise a pharmaceutically acceptable carrier and a pharmacologically effective amount of the antibodies, or mixture of antibodies.

The pharmaceutical composition may be formulated as powders, granules, solutions, suspensions, aerosols, solids, pills, tablets, capsules, gels, topical creams, suppositories, transdermal patches, and other formulations known in the art.

For the purposes described herein, pharmaceutically acceptable salts of the antibodies are intended to include any art-recognized pharmaceutically acceptable salts including organic and inorganic acids and/or bases. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. Thus, the antibodies or peptides, by themselves, such as being present as pharmaceutically acceptable salts, or as conjugates, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as solid formulations in appropriate excipients.

The pharmaceutical compositions will often further comprise one or more buffers (e.g., neutral buffered saline or phosphate buffered saline), carbohydrates (e.g., glucose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, adjuvants (e.g., aluminium hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

While any suitable carrier known to those of ordinary skill in the art may be employed in the compositions of this invention, the type of carrier will typically vary depending on the mode of administration. Antibody compositions may be formulated for any appropriate manner of administration, including for example, oral, nasal, mucosal, intravenous, intraperitoneal, intradermal, subcutaneous, and intramuscular administration.

For parenteral administration, the compositions can be administered as injectable dosages of a solution or suspension of the substance in a physiologically acceptable diluent with a pharmaceutical carrier that can be a sterile liquid such as sterile pyrogen-free water, oils, saline, glycerol, polyethylene glycol, or ethanol. Additionally, auxiliary substances, such as wetting or emulsifying agents, surfactants, pH buffering substances and the like can be present in compositions.

Other components of pharmaceutical compositions are those of petroleum, animal, vegetable, or synthetic origin, for example, non-aqueous solutions of peanut oil, soybean oil, corn oil, cottonseed oil, ethyl oleate, and isopropyl myristate. Antibodies can be administered in the form of a depot injection or implant preparation, which can be formulated in such a manner as to permit a sustained release of the active ingredient. An exemplary composition comprises antibody at 5 mg/ml, formulated in aqueous buffer consisting of 50 mM L-histidine, 150 mM NaCl, adjusted to pH 6.0 with HCl.

Typically, the compositions are prepared as injectables, either as liquid solutions or suspensions; solid or powder forms suitable for reconstitution with suitable vehicles, including by way example and not limitation, sterile pyrogen free water, saline, buffered solutions, dextrose solution, etc., prior to injection. The preparation also can be emulsified or encapsulated in liposomes or micro particles such as polylactide, polyglycolide, or copolymers.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles, as indicated above.

Alternatively, a pharmaceutical composition may be stored in a freeze-dried condition requiring only the addition of a sterile liquid carrier immediately prior to use.

Uses for Anti-TSPAN8 Antibodies

The anti-TSPAN8 antibodies of the invention have various utilities. In one embodiment, anti-TSPAN8 antibodies may be used in diagnostic or prognostic assays for TSPAN8 expression on the surfaces of different cancer cells or exomes, e.g., detecting its expression in specific cells, tissues, or serum. Various diagnostic and prognostic assay techniques known in the art may be used, such as competitive binding assays, direct or indirect sandwich assays and immunoprecipitation assays conducted in either heterogeneous or homogeneous phases (Zola, Monoclonal Antibodies: A Manual of Techniques, CRC Press, Inc. (1987) pp. 147-1581). The antibodies used in the assays can be labeled with a detectable moiety. The detectable moiety should be capable of producing, either directly or indirectly, a detectable signal. Any method known in the art for conjugating the antibody to the detectable moiety may be employed, including those methods described by Hunter et al. (1962) Nature, 144:945; David et al. (1974) Biochemistry, 13:1014; Pain et al. (1981) J. Immunol. Meth., 40:219; and Nygren, J. Histochem. and Cytochem., 30:407 (1982).

"Detecting" refers to determining the presence, absence, or amount of an analyte in a sample, and can include quantifying the amount of the analyte in a sample or per cell in a sample.

"Diagnostic" refers to identifying the presence or nature of a pathologic condition. Diagnostic methods differ in their specificity and sensitivity. While a particular diagnostic method may not provide a definitive diagnosis of a condition, it suffices if the method provides a positive indication that aids in diagnosis.

"Immunoassay" refers to a method of detecting an analyte in a sample involving contacting the sample with an antibody that specifically binds to the analyte and detecting binding between the antibody and the analyte.

"Immunohistochemical" (abbreviated IHC) refers to specific binding agents, such as polyclonal and monoclonal antibodies, which recognize and mark antigens of interest, often by a chemical that shows that the agent has bound to the antigen of interest. An example of an IHC agent is an anti-TSPAN8 monoclonal antibody.

The present invention relates to diagnostic assays, both quantitative and qualitative for detecting levels of TSPAN8 polypeptide in cells, on cell membranes, and detectable in tissues and bodily fluids, including determination of normal and abnormal levels. Assay techniques that can be used to determine levels of a polypeptide, such as TSPAN8, in a sample derived from a host are well-known to those of skill in the art. Such assay methods include, but are not limited to, radioimmunoassays, immunohistochemistry assays, in situ hybridization assays, competitive-binding assays, Western Blot analyses and ELISA assays. Among these, ELISAs are frequently used to detect a gene's expressed protein in biological fluids. An ELISA assay initially comprises preparing an antibody specific to TSPAN8, preferably a monoclonal antibody. In addition, a reporter antibody generally is prepared which binds specifically to TSPAN8. The reporter antibody is attached to a detectable reagent such as a radioactive, fluorescent or enzymatic reagent, for example horseradish peroxidase enzyme or alkaline phosphatase.

The above tests can be carried out on samples derived from patients' bodily fluids (e.g., saliva, cerebrospinal fluid, semen, interstitial fluid, amniotic fluid, etc.) and tissue extracts (homogenates or solubilized tissue) such as from tissue biopsy and autopsy material. Levels of TSPAN8, determined in cells and tissues from a patient suspected of suffering from cancer by measuring the polypeptide or by transcription levels, are compared to levels of TSPAN8 in normal or control cells or tissues. Increased levels of TSPAN8 measured in the patient as compared to levels in the same cells, tissues, or bodily fluids obtained from normal, healthy individuals (i.e., control samples) are indicative of cancer. By "increased levels" it is meant an increase in measured TSPAN8 levels in a patient as compared to TSPAN8 levels in the same normal cells or tissues. Detection of increased TSPAN8 levels is useful in the diagnosis of various cancers including, but not limited to melanoma, hepatocellular carcinoma, gastric carcinoma, colon cancer, prostate cancer, and lung cancer.

One aspect of the invention is a method to determine the likelihood of a group of cells to become cancerous e.g., for these cells or glands to become premalignancies or progress to cancerous lesions, or for determining the likelihood of a primary tumor to metastasize. The invention utilizes an agent, such as an antibody, that specifically binds to TSPAN8 protein to assess levels of TSPAN8 in tissue and cells. TSPAN8 expression in cells and tissue may also be assessed using nucleic acid analysis, such as selective amplification, or hybridization methods. A level of TSPAN8 greater than normal or control levels, indicates an increased likelihood that premalignant disease is present i.e., that the cells or tissues are premalignant, and/or that a primary tumor is likely to metastasize.

In another embodiment, the anti-TSPAN8 antibodies are useful for a method of treatment of a disease, such as cancer. The method of the invention preferably includes the step of providing an antibody or TSPAN8 antigen-binding fragment thereof, as described above, to a subject requiring said treatment.

Methods of immunotargeting cancer cells using antibodies or antibody fragments are well known in the art. U.S. Pat. No. 6,306,393, for instance, describes the use of anti-CD22 antibodies in the immunotherapy of B-cell malignancies, and U.S. Pat. No. 6,329,503 describes immunotargeting of cells that express serpentine transmembrane antigens. Antibodies described herein (including humanized or human monoclonal antibodies or fragments or other modifications thereof, optionally conjugated to cytotoxic or other agents) can be introduced into a patient such that the antibody binds to cancer cells and mediates the destruction of the cells and the tumor and/or inhibits the growth of the cells or the tumor.

Without intending to limit the disclosure, mechanisms by which such antibodies can exert a therapeutic effect may include complement-mediated cytolysis, antibody-dependent cellular cytotoxicity (ADCC) modulating the physiologic function of the tumor antigen, inhibiting binding or signal transduction pathways, modulating tumor cell differentiation, altering tumor angiogenesis factor profiles, modulating the secretion of immune stimulating or tumor suppressing cytokines and growth factors, modulating cellular adhesion, and/or by inducing apoptosis.

The antibodies can also be conjugated to toxic or therapeutic agents, such as radioligands, dyes, fluorescent and/or luminescent agents, or cytosolic toxins, and may also be used therapeutically to deliver the toxic or therapeutic agent directly to tumor cells. Moreover, in some embodiments of the invention, the labeled antibodies may be used to label cells in vivo or in vitro to determine levels of expression of TSPAN8 protein. As such, the labeled cells may be directly or indirectly imaged via secondary methods that are applicable to each labeling agent.

By "treatment" herein is meant therapeutic, prophylactic, palliative, or suppressive treatment for the disease, disorder or undesirable condition. Treatment encompasses administration of the subject antibodies in an appropriate form prior to the onset of disease symptoms and/or after clinical manifestations, or other manifestations, of the disease to reduce disease severity, halt disease progression, or eliminate the disease. Prevention of the disease includes prolonging or delaying the onset of symptoms of the disorder or disease, preferably in a subject with increased susceptibility to the disease.

The therapeutic preparations can use non-modified antibodies or antibodies conjugated with a therapeutic compound, such as a toxin or cytotoxic molecule, depending on the functionality of the antibody. Generally, when non-modified antibodies are used, they will typically have a functional Fc region. By "functional Fc region" herein is meant a minimal sequence for affecting the biological function of Fc, such as binding to Fc receptors, particularly FcγR (e.g., Fcγ RI, FcγRII, and FcγRIII).

Without being bound by theory, it is believed that the Fc region may affect the effectiveness of anti-tumor monoclonal antibodies by binding to Fc receptors immune effector cells and modulating cell mediated cytotoxicity, endocytosis, phagocytosis, release of inflammatory cytokines, complement mediate cytotoxicity, and antigen presentation. In this regard, polyclonal antibodies, or mixtures of monoclonal antibodies will be advantageous because they will bind to different epitopes and thus have a higher density of Fc on the cell surface as compared to when a single monoclonal antibody is used. Of course, to enhance their effectiveness in depleting targeted cells, or where non-modified antibodies are not therapeutically effective, antibodies conjugated to toxins or cytotoxic agents may be used.

The antibody compositions may be used either alone or in combination with other therapeutic agents to increase efficacy of traditional treatments or to target abnormal cells not targeted by the antibodies. The antibodies and antibody compositions of the invention include PEGylated antibodies and/or pretargeting constructs of the antibodies. Combining the antibody therapy method with a chemotherapeutic, radiation or surgical regimen may be preferred in patients that have not received chemotherapeutic treatment, whereas treatment with the antibody therapy may be indicated for patients who have received one or more chemotherapies. Additionally, antibody therapy can also enable the use of reduced dosages of concomitant chemotherapy, particularly in patients that do not tolerate the toxicity of the chemotherapeutic agent very well. Furthermore, treatment of cancer patients with the antibody with tumors resistant to chemotherapeutic agents might induce sensitivity and responsiveness to these agents in combination.

In one aspect, the antibodies are used adjunctively with therapeutic cytotoxic agents, including, by way of example and not limitation, busulfan, thioguanine, idarubicin, cytosine arabinoside, 6-mercaptopurine, doxorubicin, daunorubicin, etoposide, and hydroxyurea. Other agents useful as adjuncts to antibody therapy are compounds directed specifically to the abnormal cellular molecule found in the disease state. These agents will be disease specific.

The amount of the compositions needed for achieving a therapeutic effect will be determined empirically in accordance with conventional procedures for the particular purpose. Generally, for administering the compositions ex vivo or in vivo for therapeutic purposes, the compositions are given at a pharmacologically effective dose. By "pharmacologically effective amount" or "pharmacologically effective dose" is an amount sufficient to produce the desired physiological effect or amount capable of achieving the desired result, particularly for treating or retreating the disorder or disease condition, including reducing or eliminating one or more symptoms or manifestations of the disorder or disease.

As an illustration, administration of antibodies to a patient suffering from breast cancer provides a therapeutic benefit not only when the underlying disease is eradicated or ameliorated, but also when the patient reports a decrease in the severity or duration of the symptoms associated with the disease. Therapeutic benefit also includes halting or slowing the progression of the underlying disease or disorder, regardless of whether improvement is realized.

The amount administered to the subject will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but is not limited to, size and weight of the subject, the age and sex of the subject, the severity of the symptom, the stage of the disease, method of delivery of the agent, half-life of the agents, and efficacy of the agents. Stage of the disease to consider includes whether the disease is acute or chronic, relapsing or remitting phase, and the progressiveness of the disease. Determining the dosages and times of administration for a therapeutically effective amount is well within the skill of the ordinary person in the art.

For any compositions of the present disclosure, the therapeutically effective dose is readily determined by methods well known in the art. For example, an initial effective dose can be estimated from cell culture or other in vitro assays. For example, Sliwkowsky, M X et al. (1999) Semin. Oncol. 26.suppl. 12: 60-70 describes in vitro measurements of antibody dependent cellular cytotoxicity. A dose can then be formulated in animal models to generate a circulating concentration or tissue concentration, including that of the $IC_{50}$ as determined by the cell culture assays.

In addition, the toxicity and therapeutic efficacy are generally determined by cell culture assays and/or experimental animals, typically by determining a $LD_{50}$ (lethal dose to 50% of the test population) and $ED_{50}$ (therapeutically effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art, particularly given the detailed disclosure provided herein. Guidance is also found in standard reference works, for example Fingl and Woodbury, General Principles In: The Pharmaceutical Basis of Therapeutics pp. 1-46 (1975), and the references cited therein.

To achieve an initial tolerizing dose, consideration is given to the possibility that the antibodies may be immunogenic in humans and in non-human primates. The immune response may be biologically significant and may impair the therapeutic efficacy of the antibody even if the antibody is partly or chiefly comprised of human immunoglobulin sequences such as, for example, in the case of a chimeric or humanized antibody. Within certain embodiments, an initial high dose of antibody is administered such that a degree of immunological tolerance to the therapeutic antibody is established.

The tolerizing dose is sufficient to prevent or reduce the induction of an antibody response to repeat administration of the committed progenitor cell specific antibody.

Preferred ranges for the tolerizing dose are between 10 mg/kg body weight to 50 mg/kg body weight, inclusive. More preferred ranges for the tolerizing dose are between 20 and 40 mg/kg, inclusive. Still more preferred ranges for the tolerizing dose are between 20 and 25 mg/kg, inclusive.

Within these therapeutic regimens, the therapeutically effective dose of antibodies is preferably administered in the range of 0.1 to 10 mg/kg body weight, inclusive. More preferred second therapeutically effective doses are in the range of 0.2 to 5 mg/kg body weight, inclusive. Still more preferred therapeutically effective doses are in the range of 0.5 to 2 mg/kg, inclusive. Within alternative embodiments, the subsequent therapeutic dose or doses may be in the same or different formulation as the tolerizing dose and/or may be administered by the same or different route as the tolerizing dose.

For the purposes of this invention, the methods of administration are chosen depending on the condition being treated, the form of the subject antibodies, and the pharmaceutical composition.

Administration of the antibody compositions can be done in a variety of ways, including, but not limited to, continuously, subcutaneously, intravenously, orally, topically, transdermal, intraperitoneal, intramuscularly, and intravesically. For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, intraperitoneal administration can be accompanied by intravenous injections. Preferably the therapeutic doses are administered intravenously, intraperitonealy, intramuscularly, or subcutaneously.

The compositions may be administered once or several times. In some embodiments, the compositions may be administered once per day, a few or several times per day, or even multiple times per day, depending upon, among other things, the indication being treated and the judgment of the prescribing physician.

Administration of the compositions may also be achieved through sustained release or long-term delivery methods, which are well known to those skilled in the art. By "sustained release or" "long-term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the antibodies, such as biodegradable polymers described above; pumps, including peristaltic pumps and fluorocarbon propellant pumps; osmotic and mini-osmotic pumps; and the like.

The method of the invention contemplates the administration of single monoclonal antibodies and any antibody that recognizes the particular antigens recognized by these antibodies, as well as combinations, of different monoclonal antibodies. Two or more monoclonal antibodies may provide an improved effect compared to a single antibody. Alternatively, a combination of an antibody with an antibody that binds a different antigen may provide an improved effect compared to a single antibody. Additionally, contrast agents may be administered in combination with the antibodies in order to improve differential labeling of neoplastic cells or lesions. Such monoclonal antibodies cocktails may have certain advantages inasmuch as they contain monoclonal antibodies, which exploit different effector mechanisms or combine directly cytotoxic monoclonal antibodies with monoclonal antibodies that rely on immune effector functionality. Such monoclonal antibodies in combination may exhibit synergistic therapeutic effects.

Some embodiments of the present invention may also be used to isolate, collect, and/or otherwise purify components of tissues and/or cells. Some embodiments provide a method of isolating cells and/or byproducts, components, including components released from the cells (e.g., exosomes), and/or other portions of cells. In one embodiment, the anti-TSPAN8 antibodies can be used in isolating cells and/or components of cells. For example, as described above, TSPAN8 is a transmembrane protein with two extracellular domains, EC1 and EC2. In some aspects, the anti-TSPAN8 antibodies can specifically bind to one or both EC1 and EC2. As such, the monoclonal antibodies of the invention can be used to bind to TSPAN8 anchored in the cell membrane for selection of these cells and/or cell components.

Monoclonal antibodies of the present invention can be used to isolate exosomes. For example, embodiments of the invention provide a method of isolating exosomes. As previously mentioned, exosomes often comprise native TSPAN8 anchored in the membrane. Accordingly, anti-TSPAN8 monoclonal antibodies can be added to a mixture comprising exosomes and allowed to bind to TSPAN8 anchored in the membrane of the exosomes and selected for purification. In some aspects, the anti-TSPAN8 antibodies may be modified to provide for a method of purification. For example, the anti-TSPAN8 antibodies may comprise one or more biotin moieties such that the antibodies are "biotinylated." After binding to the TSPAN8 anchored in the membrane of the exosomes, the biotinylated antibodies-exosome product can be passed over and/or through a streptavidin reagent (e.g., a streptavidin column or filter), which will engage the biotin moieties on the anti-TSPAN8 antibodies. Thereafter, the biotin and streptavidin can be separated to produce a relatively or completely pure population of exosomes. In other embodiments, any other mechanism of purification known in the art can be used with the anti-TSPAN8 monoclonal antibodies. For example, a magnetic bead coupled to the anti-TSPAN8 antibody can be used in conjunction with a magnetic field to isolate exosomes. In other aspects, the anti-TSPAN8 antibodies can be labeled (e.g., fluorescently labeled) and flow cytometry and/or fluorescence-activated cell sorting can be used to isolate the labeled exosomes.

Antibody Kits

Antibody kits are provided which contain the necessary reagents to carry out the assays of the present invention. The kit may include one or more compartments, each to receive one or, more containers such as: (a) a first container comprising one of the components of the present invention described above; and (b) one or more other containers comprising one or more of the following: wash reagents, reagents capable of detecting presence of the antibody or peptide, and/or recombinant TSPAN8 protein or fragments thereof as a control for detection or for a competitive assay. For example, in some embodiments, the kit can be configured as an exosome-purification kit.

The containers allow one to efficiently transfer reagents from one compartment to another compartment such that the samples and reagents are not cross-contaminated, and the agents or solutions of each container can be added in a quantitative fashion from one compartment to another.

The kit typically contains containers, which may be formed from a variety of materials such as glass or plastic, and can include for example, bottles, vials, syringes, and test tubes. A label typically accompanies the kit, and includes any writing or recorded material, which may be electronic or computer readable form (e.g., disk, optical disc, or tape) providing instructions or other information for used of the contents of the kit. The label indicates that the formulation is used for diagnosing or treating the disorder of choice or provides instructions regarding exosome purification methods.

One skilled in the art will readily recognize that the disclosed antibodies of the present invention can be readily incorporated into one of the established kit formats, which are well known in the art.

All patent and literature references cited in the present specification are hereby incorporated by reference in their entirety.

The following examples are offered for illustrative purposes only, and are not intended to limit the scope of the present invention in any way.

EXAMPLES

Multiple murine hybridoma clones that secrete murine monoclonal antibodies that bind to the human TSPAN8 protein were generated. As described in greater detail herein, these antibodies recognize (e.g., specifically bind) human TSPAN8 in its native form or fragments thereof.

Commercially available reagents referred to in the examples were used according to manufacturer's instructions unless otherwise indicated. The following examples are offered for illustrative purposes only, and are not intended to limit the scope of the present invention in any way.

Example 1

General Hybridoma Production and Screening Protocol

The following protocols are used for general hybridoma production in the laboratory, as well as for screening and subcloning hybridomas.

General Hybridoma Fusion Protocol

Fusion Preparation:

3-4 Days Prior to Fusion

1) Two T-75 or one T-225 flask of myeloma cells, P3X653 (P3 cells), at $5 \times 10^5$ cell/ml (50 ml) in 10% C-DMEM were set up. Fresh media was added the day before fusion. In addition, during this timeframe, the animals that were used to generate desired lymphocytes for fusion received an intravenous booster injection. Moreover, any equipment that was to be used in harvesting tissue from the animals was autoclaved.

Day of the Fusion

On the day of fusion, Fusion Media was prepared as follows: DMEM (LTI) 128 ml, HAT (50×; Sigma) 4 ml, OPI (100×: Sigma) 2 ml, HEPES (1 M; Sigma) 2 ml, Glutamax I (100×; LTI) 2 ml, NCTC (Sigma) 20 ml, FBS (LTI) 40 ml, Pen/Strep (LTI) 2 ml, Nutridoma (BM) 2.0 ml. In addition, 50 ml of SF-DMEM with 0.5 ml of 1 M HEPES (DMEM/HEPES) was prepared. Thereafter, 9.5 ml of DMEM/HEPES and 0.5 ml DMSO was added to a conical tube (DMEM/HEPES/DMSO).

After preparation of the aforementioned media, the following were placed in a 37° C. water bath: 200 ml Fusion Media (FX-media), 40 ml DMEM/HEPES, 10 ml DMEM/HEPES/DMSO, and 1 ml aliquot of polyethylene glycol/DMSO mix (PEG/DMSO). In addition, eight flat bottom 96 well plates were labeled with fusion number, plate number, and date (e.g., FX03.5 8/31/07) Further, 50×HAT was suspended in 10 mL of SF-DMEM and 100×OPI was suspend in 10 mL sterile water.

Fusion

Figure 2:
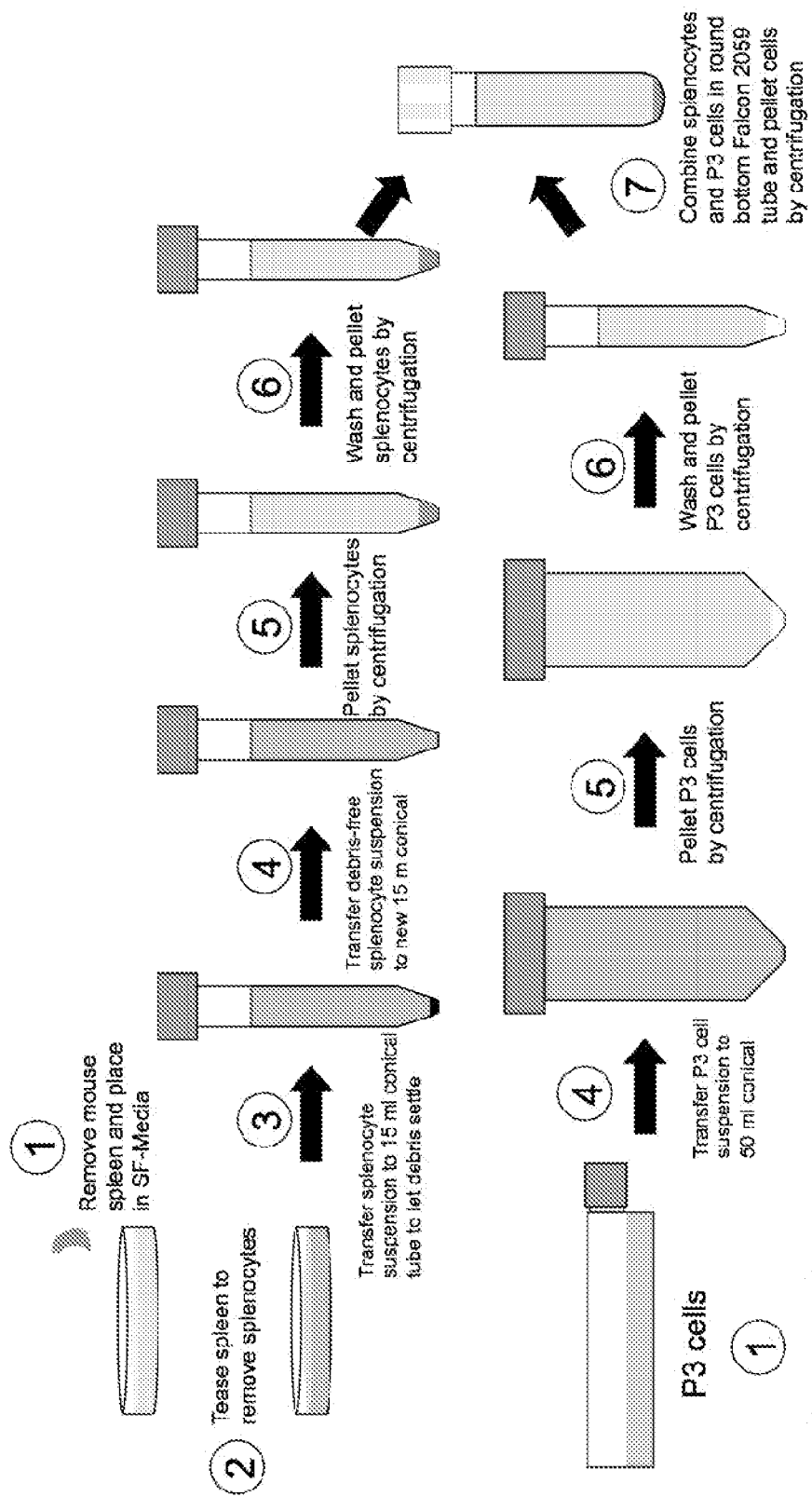
FIG. 2 illustrates the steps taken to produce hyrbidomas disclosed herein.

FIG. 2 illustrates the steps that can be employed in the fusion process. Initially, mice that have been previously immunized with an antigen (as described in greater detail below) were sacrificed and spleens were removed. Each spleen was placed in 10 ml DMEM/HEPES in a 100 mm cell culture dish. In addition, P3 cells were harvested and counted such that between 5 and $20 \times 10^7$ cells were used for fusion.

Once the spleens were placed in the cell culture dish, the splenocytes were removed by teasing the spleen and the resulting splenic cell suspension was placed in a 15 ml conical tube and large debris was allowed to settle for 2-3 minutes. At this time, the counted P3 cells were transferred to a 50 ml conical tube. In addition, the splenic-cell suspension was removed from the 15 ml conical tube, leaving behind the large debris and transferred to a new 15 ml conical tube. The splenic-cell suspension and the P3 cells were respectively pelleted by centrifugation.

Thereafter, the splenic cells (i.e., splenocytes) were washed with 10 ml of warm DMEM/HEPES, with gentle mixing to enable clots to stick to the pipet used to suspend the pelleted splenic cells. The P3 cells were also washed in 10 ml of DMEM/HEPES. The P3 cells and the splenic cells were again pelleted and respectively suspended in 5 ml each of warm DMEM/HEPES and mixed together in a 14 ml round-bottom tube (Falcon® 2059). The mixed-cell suspension was pelleted and the resulting supernatant was removed by aspiration. The resulting mixed-cell pellet was gently disrupted and incubated at 37° C. for 1-2 minutes.

In order to induce fusion of the splenic cells and P3 cells, 1 ml of 50% PEG/DMSO (Sigma) was added over 45-60 seconds with constant stirring and flicking. The cell suspension was then swirled at 37° C. for 45 seconds. After this incubation, the PEG was diluted out by adding 2 ml of warm DMEM/HEPES/5% DMSO over 2 minutes in the same manner as the PEG (i.e., stirring, flicking, and swirling at 37° C.). After this addition, the mixture was further diluted by adding 8 ml of DMEM/HEPES/DMSO over 2 minutes and the fused cells were incubated for 15 minutes at 37° C. After the incubation, the fused cells were pelleted and suspended in 160 ml of fusion medium with freshly added Nutridoma. The resulting mixture was plated at 200 µl/well and incubated in a plastic container at 37° C.

Screening of Fused Cells

Primary Screen

Initially, two 384-well plates were coated with 25 µl per well of approximately 0.5 µg/ml of the protein of interest (e.g., native TSPAN8 polypeptide or a fragment thereof that has been conjugated to glutathione) in coating buffer (50 mM Tris-Cl, pH 9.5). These two 384-well plates were incubated overnight at 4° C.

On the day of the screening, the coating comprising the protein of interest was removed and 50 µl per well of blocking buffer (1% BSA) was added and the plates were incubated for 30 min at 37° C. Thereafter, 25 µl from each well from the fusion plates was added and incubated for 1 hr at room temperature (RT). The wells were then washed three times with 50 µl/well of PBS-Tween (PBS-T). After the washing step, 25 µl of 1 µg/ml horseradish peroxidase-conjugated-GAM (an anti-mouse antibody of goat origin) Fc in PBS-T was added to each well and incubated for 1 hr at RT. Each well was then washed three times with 50 µl/well of PBS-T. After the washing step, 25 µl of OPD substrate (Pierce) with 0.1% hydrogen peroxide was added to each well and incubated for 15 min at RT. After incubation, 25 µl of STOP buffer (2 M sulfuric acid) was added to each well and the absorbance from each well was reach at 495 nM. Thereafter, the resulting data was analyzed using 384-well spreadsheet to determine which hybridomas produced antibodies that bind to the protein of interest.

Example 2

Experimental Methods

Production of Monoclonal Antibodies to TSPAN8

Monoclonal antibodies (mAbs) were generated as previously described (Azorsa et al. (1999) *J Immunol Methods* 229:35-48) with the following modifications: Female Balb/c mice (6-8 weeks old) were injected with 3-5 million fixed LoVo colorectal cancer cells (ATCC CCL-229) in PBS via intraperitoneal injection 3 times at 2-week intervals, followed by injections of 3-5 million fixed LoVo colorectal cancer cells in PBS for three consecutive days. LoVo colorectal cells are known to express TSPAN8. Splenocytes were isolated and fused to the myeloma cell line P3×653 using PEG:DMSO (50:5, % v, Sigma-Aldrich), as described above. Fused cells were seeded in 96-well plates in DMEM: NCTC-109 (90:10, % v, Invitrogen, Carlsbad, Calif.) media supplemented with 20% FBS (Invitrogen), 2 mM Glutamax I (Invitrogen), 25 mM Hepes, 1×HAT (Sigma-Aldrich), Penicillin/Streptomycin, and 0.5× Nutridoma-CS (Roche, Branchburg, N.J.). Hybridoma colonies were screened by ELISA and were subcloned twice by limiting-dilution. Tissue culture supernatant from one hybridoma clone containing anti-TSPAN8 mAbs termed BT-43 was collected and stored with 0.02% sodium azide at 4° C.

A hybridoma expressing monoclonal antibodies that specifically binds to human TSPAN8 protein, as described above and below, was deposited with the American Type Tissue Culture Collection (ATCC; 10801 University Blvd, Manassas Va. 20110-2209) patent depository as original deposits under the Budapest Treaty and was given the following ATCC Accession No: clone BT-43 (ATCC Patent Deposit Designation PTA-121023, deposited Feb. 26, 2014).

Specificity of anti-TSPAN8 Monoclonal Antibody

The monoclonal antibody was screened as previously described in Azorsa et al. (1999) *J Immunol Methods* 229:35-48. Briefly, recombinant glutathione (GST) constructs expressing the extracellular domain 2 (EC2) from six different tetraspanins were used to assess the binding specificity of the anti-TSPAN8 monoclonal antibody (clone BT-43). In particular, the six tetraspanins were CD9, CD63, CD81, CD82, A15/TALLA-1 (TSPAN7), and TSPAN8. These GST-EC2 domains and GST controls were plated on a 96-well ELISA plate and treated with BT-43 hybridoma culture, supernatant containing the secreted BT-43 monoclonal antibody (anti-TSPAN8). The supernatant was allowed to incubate at one hour at room temperature. The wells of the ELISA plate were washed three times with PBS-Tween. After washing, a secondary antibody (5 µg/ml horseradish-peroxidase conjugated goat anti-mouse Fc from Jackson Immunoresearch) was added to each well and incubated for one hour at room temperature. The wells of the plate were again washed three times with PBS-Tween. After the washing, 50 µl of substrate (OPD from Pierce) was added for 5-10 minutes. The reaction was stopped by the addition of 25 µl of 2M $H_2SO_4$. The absorbance of the resulting solutions in each well was read at 490 nm.

Immunofluorescent Staining and Western Blot Analysis

Pancreatic cancer cell line AsPC1 is known to express TSPAN8. AsPC1 cells were plated on chamber slides and allowed to grow to 50% confluency and fixed with 4% paraformaldehyde. Cells were immunostained with hybridoma supernatant containing anti-TSPAN8 antibody (BT-43, 1:10 dilution) followed by Cy3-conjugated goat anti-mouse secondary antibody (1:200, Jackson Immunoresearch, West Grove, Pa.). Cells were visualized using a fluorescent microscope. For Western blot analysis, AsPC1 cells were lysed and the resulting lysate was run on a non-reducing acrylamide gel. For probing the lysate, hybridoma supernatant containing anti-TSPAN8 antibody (BT-43) was used in 1:10 dilution. The Western blot was performed using techniques known in the art.

Example 3

Screening of Monoclonal Anti-TSPAN8 Antibody

Figure 3:
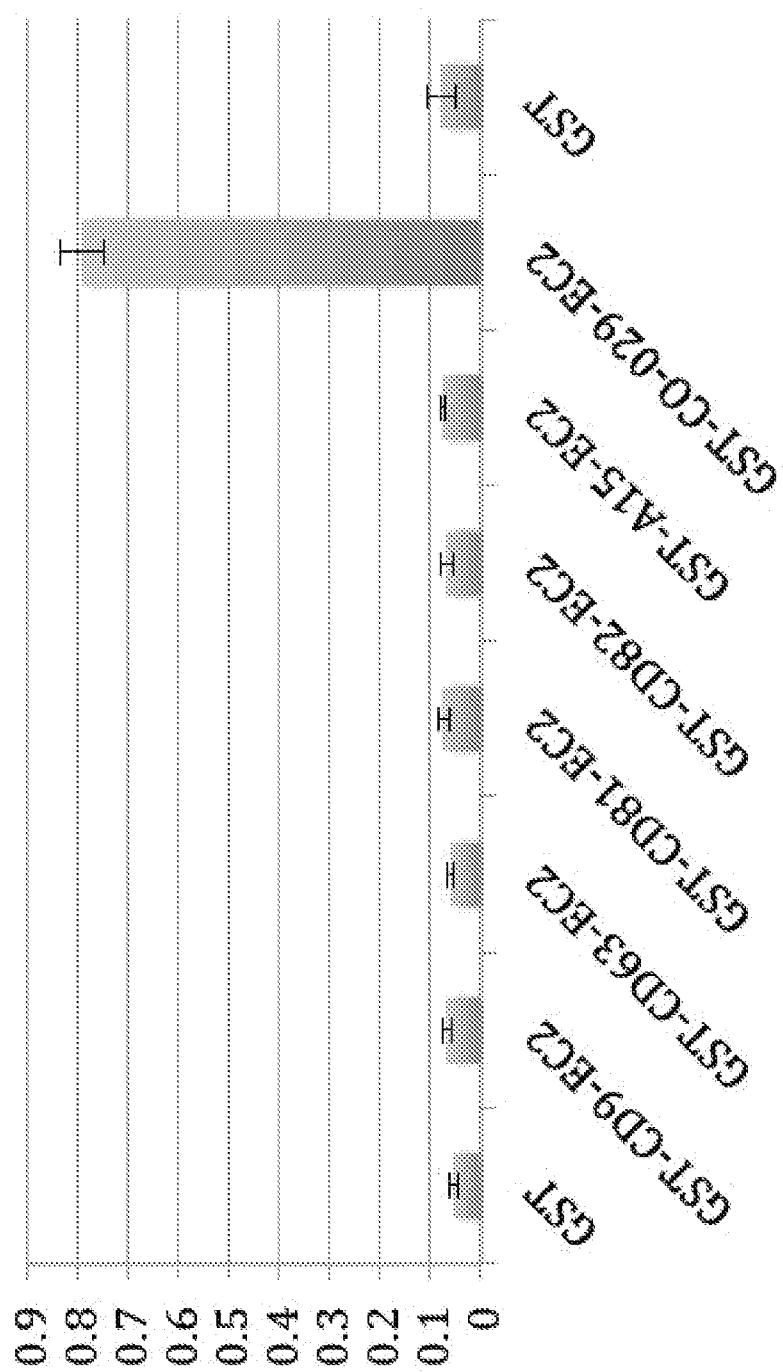
FIG. 3 is a bar graph illustrating the results of experiments conducted to elucidate the binding specificity of the BT-43 monoclonal antibody. In these experiments, the binding specificity of the BT-43 monoclonal antibody was measured using the extracellular domains (EC2) of the following related tetraspanins: CD9, CD63, CD81, CD82, A15 (TSPAN7), and TSPAN8. The results indicate that BT-43 monoclonal antibody binds specifically to TSPAN8 EC2.

Initially, experiments were conducted to assess the specificity of the BT-43 clone/anti-TSPAN8 monoclonal antibody by using a recombinant GST protein expressing the EC2 domain of TSPAN8 (SEQ ID NO:2). Specificity experiments were conducted to ensure that there was no cross-reactivity between the BT-43 monoclonal antibody and EC2 domains from other tetraspanins. In these experiments, recombinant EC2 domains from six tetraspanins (CD9, CD63, CD81, CD82, A15/TALLA-1 (TSPAN7), and TSPAN8) were used in a sandwich assay (ELISA) to test the specificity of the BT-43 antibody. As illustrated in FIG. 3, no significant binding of the BT-43 antibody was detected for any of the conditions/EC2 domains other than the TSPAN8 EC2 domain. As such, this data illustrates that the BT-43 monoclonal antibody binds exclusively to native TSPAN8 polypeptide (SEQ ID NO:1) and specifically to the EC2 domain (SEQ ID NO:2).

Figure 4A:
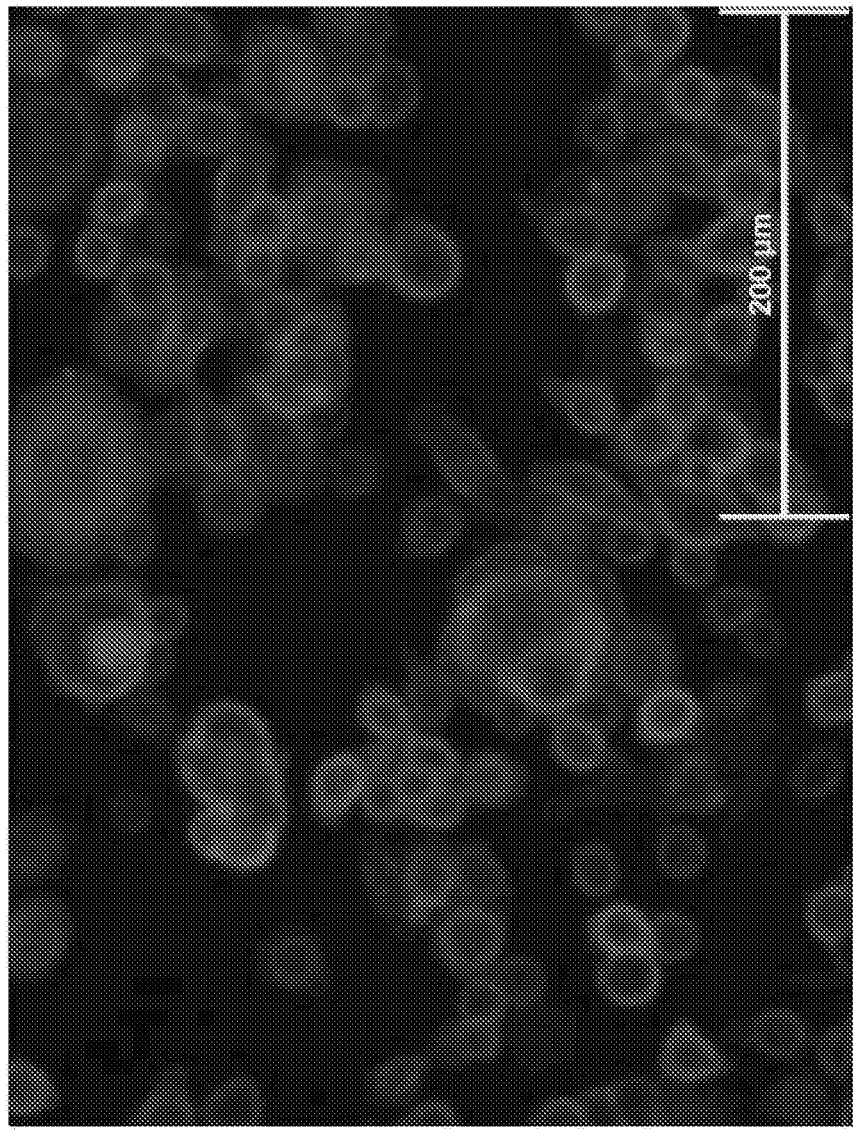
FIG. 4A is an image from an immunofluorescence staining experiment in which the binding specificity of the BT-43 monoclonal antibody was further validated. AsPC1 cells, human pancreatic cancer cells known to express membrane-bound TSPAN8, were grown, fixed, and stained with BT-43 monoclonal antibody. The resulting images show staining localized at the cell membrane, which is expected because TSPAN8 is a transmembrane protein.
Figure 4B:
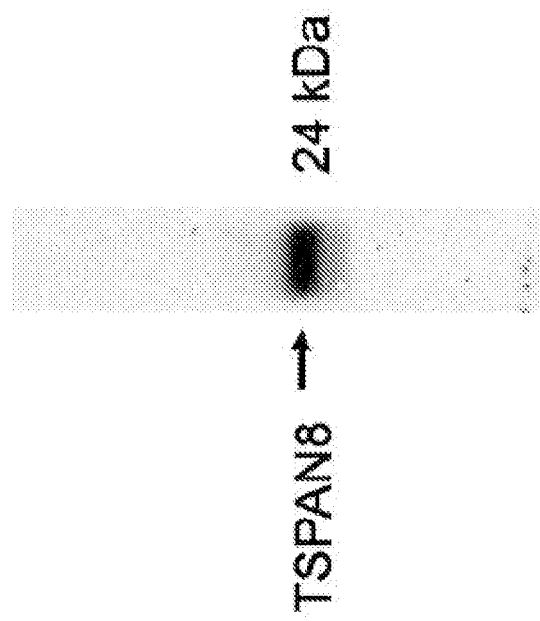
FIG. 4B is an image of a Western blot in which the binding specificity of the BT-43 monoclonal antibody was further validated. AsPC1 cells were lysed and the resulting lysate was run on a non-reducing polyacrylamide gel. The lysate was probed with BT-43 monoclonal antibody. The blot shows specific staining of TSPAN8 at the expected location (about 24 kDa).

Next, the BT-43 monoclonal antibody binding specificity data was further validated using the AsPC1 cell line. This cell line, which is an immortalized human pancreatic cancer cell line, is known to express TSPAN8 on its surface. As such, whole AsPC1 cells were immunostained and AsPC1 cell lysates were probed using the BT-43 monoclonal antibody. Referring to FIG. 4A, whole fixed AsPC1 cells positively stained for TSPAN8 using the BT-43 monoclonal antibody. Moreover, from the immunofluorescence image, it is clear that the strongest staining is at the cell membrane, which is where a significant portion of the TSPAN8 should be localized. This immunofluorescence data further illustrates that the BT-43 monoclonal antibody specifically binds to human TSPAN8 protein. Referring now to FIG. 4B, AsPC1 cell lysate that is run on a non-reducing polyacrylamide gel probed with BT-43 monoclonal antibody also shows the specificity of this anti-TSPAN8 antibody for native TSPAN8 polypeptide. Taken together, these results demonstrate the specific binding of the BT-43 monoclonal antibody to the native human TSPAN8 polypeptide/protein.

Having herein set forth the various embodiments of the present invention, it is anticipated that suitable modifications can be made thereto which will nonetheless remain within the scope of the invention. The invention shall therefore only be construed in accordance with the following claims below.

What is claimed is:

1. A monoclonal antibody that binds to a human TSPAN8 protein, wherein the monoclonal antibody is produced by hybridoma cell line BT-43, ATCC accession number PTA-121023.

2. The monoclonal antibody of claim 1, wherein the monoclonal antibody specifically binds to the amino acid sequence of SEQ ID NO:1.

3. The monoclonal antibody of claim 1, wherein the antibody is an IgG1, kappa chain isotype.

4. The monoclonal antibody of claim 1, wherein the antibody is labeled.

5. The monoclonal antibody of claim 4, wherein the antibody is labeled with one or more labels selected from the group consisting of a biotin label, a fluorescent label, an enzyme label, a coenzyme label, a chemiluminescent label, and a radioactive isotope label.

6. The monoclonal antibody of claim 1, wherein the monoclonal antibody specifically binds to the amino acid sequence of SEQ ID NO:2.

7. An isolated monoclonal antibody produced by hybridoma cell line BT-43, ATCC accession number PTA-121023.

8. The monoclonal antibody of claim 7, wherein the monoclonal antibody specifically binds to the amino acid sequence of SEQ ID NO:1.

9. The monoclonal antibody of claim 7, wherein the antibody is an IgG1, kappa chain isotype.

10. The monoclonal antibody of claim 7, wherein the antibody is labeled.

11. The monoclonal antibody of claim 10, wherein the antibody is labeled with one or more labels selected from the group consisting of a biotin label, a fluorescent label, an enzyme label, a coenzyme label, a chemiluminescent label, and a radioactive isotope label.

12. The monoclonal antibody of claim 7, wherein the monoclonal antibody specifically binds to the amino acid sequence of SEQ ID NO:2.

13. A method of making a monoclonal antibody, the method comprising providing hybridoma cell line BT-43, ATCC accession number PTA-121023, which produces a monoclonal antibody specific for human tetraspanin 8, and culturing the hybridoma cell line BT-43 under conditions that permit the production of the monoclonal antibody.

14. The method of claim 13 and further comprising coupling a label to the monoclonal antibody.

15. The method of claim 14, wherein the label is selected from the group consisting of a biotin label, a fluorescent label, an enzyme label, a coenzyme label, a chemiluminescent label, and a radioactive isotope label.

16. The method of claim 13, wherein the monoclonal antibody specifically binds to the amino acid sequence of SEQ ID NO:2.

17. An exosome purification kit comprising at least one container containing a monoclonal antibody produced by a hybridoma cell line of BT-43, ATCC accession number PTA-121023.

18. The exosome purification kit of claim 17, wherein the monoclonal antibody is labeled.

19. The exosome purification kit of claim 18, wherein the antibody is labeled with one or more labels selected from the group consisting of a biotin label, a fluorescent label, an enzyme label, a coenzyme label, a chemiluminescent label, and a radioactive isotope label.

* * * * *

SEQUENCE LISTING

```
<160> NUMBER OF SEQ ID NOS: 2

<210> SEQ ID NO 1
<211> LENGTH: 237
<212> TYPE: PRT
<213> ORGANISM: Homo sapiens

<400> SEQUENCE: 1

Met Ala Gly Val Ser Ala Cys Ile Lys Tyr Ser Met Phe Thr Phe Asn
1               5                   10                  15

Phe Leu Phe Trp Leu Cys Gly Ile Leu Ile Leu Ala Leu Ala Ile Trp
            20                  25                  30

Val Arg Val Ser Asn Asp Ser Gln Ala Ile Phe Gly Ser Glu Asp Val
        35                  40                  45

Gly Ser Ser Ser Tyr Val Ala Val Asp Ile Leu Ile Ala Val Gly Ala
    50                  55                  60

Ile Ile Met Ile Leu Gly Phe Leu Gly Cys Cys Gly Ala Ile Lys Glu
65                  70                  75                  80

Ser Arg Cys Met Leu Leu Leu Phe Phe Ile Gly Leu Leu Leu Ile Leu
                85                  90                  95

Leu Leu Gln Val Ala Thr Gly Ile Leu Gly Ala Val Phe Lys Ser Lys
            100                 105                 110

Ser Asp Arg Ile Val Asn Glu Thr Leu Tyr Glu Asn Thr Lys Leu Leu
        115                 120                 125

Ser Ala Thr Gly Glu Ser Glu Lys Gln Phe Gln Glu Ala Ile Ile Val
    130                 135                 140

Phe Gln Glu Glu Phe Lys Cys Cys Gly Leu Val Asn Gly Ala Ala Asp
145                 150                 155                 160

Trp Gly Asn Asn Phe Gln His Tyr Pro Glu Leu Cys Ala Cys Leu Asp
                165                 170                 175

Lys Gln Arg Pro Cys Gln Ser Tyr Asn Gly Lys Gln Val Tyr Lys Glu
            180                 185                 190

Thr Cys Ile Ser Phe Ile Lys Asp Phe Leu Ala Lys Asn Leu Ile Ile
        195                 200                 205

Val Ile Gly Ile Ser Phe Gly Leu Ala Val Ile Glu Ile Leu Gly Leu
    210                 215                 220

Val Phe Ser Met Val Leu Tyr Cys Gln Ile Gly Asn Lys
225                 230                 235
```

```
<210> SEQ ID NO 2
<211> LENGTH: 96
<212> TYPE: PRT
<213> ORGANISM: Homo sapiens

<400> SEQUENCE: 2

Lys Ser Lys Ser Asp Arg Ile Val Asn Glu Thr Leu Tyr Glu Asn Thr
1               5                   10                  15

Lys Leu Leu Ser Ala Thr Gly Glu Ser Glu Lys Gln Phe Gln Glu Ala
            20                  25                  30

Ile Ile Val Phe Gln Glu Glu Phe Lys Cys Cys Gly Leu Val Asn Gly
        35                  40                  45

Ala Ala Asp Trp Gly Asn Asn Phe Gln His Tyr Pro Glu Leu Cys Ala
    50                  55                  60

Cys Leu Asp Lys Gln Arg Pro Cys Gln Ser Tyr Asn Gly Lys Gln Val
65                  70                  75                  80

Tyr Lys Glu Thr Cys Ile Ser Phe Ile Lys Asp Phe Leu Ala Lys Asn
                85                  90                  95
```